United States Patent [19]
Levine et al.

[11] Patent Number: 6,126,959
[45] Date of Patent: Oct. 3, 2000

[54] PHARMACEUTICAL COMPOSITION FOR TREATING DYSMENORRHEA AND PREMATURE LABOR

[75] Inventors: Howard L. Levine, Oceanside; William J. Bologna, New York, both of N.Y.; Dominique de Ziegler, Paris, France

[73] Assignee: Columbia Laboratories, Inc., Aventura, Fla.

[21] Appl. No.: 09/145,172

[22] Filed: Sep. 1, 1998

Related U.S. Application Data

[60] Provisional application No. 60/058,789, Sep. 12, 1997.

[51] Int. Cl.$^7$ .............................. A61F 13/02; A61F 6/06
[52] U.S. Cl. ...................... 424/434; 424/430; 514/772.6
[58] Field of Search .................................. 424/430, 434; 514/772.6

[56] References Cited

U.S. PATENT DOCUMENTS

| 4,615,697 | 10/1986 | Robinson . |
| 5,543,150 | 8/1996 | Bologna et al. . |

FOREIGN PATENT DOCUMENTS

| 0 147 780 | 7/1985 | European Pat. Off. . |
| 2 720 276 | 12/1995 | France . |
| WO 93/00058 | 1/1993 | WIPO . |
| WO 95/07699 | 3/1995 | WIPO . |
| WO 96/10989 | 4/1996 | WIPO . |
| WO 98/23292 | 6/1998 | WIPO . |
| WO 98/56323 | 12/1998 | WIPO . |

OTHER PUBLICATIONS

Lalos, O. et al., "Effect of salbutamol on the non–pregnant human uterus in vivo", Acta Obstet Gynecol Scand, vol. 60, No. 4 (1981), 349–352.

Lockwood, C.J., "The diagnosis of preterm labor and the prediction of preterm delivery," Clinical Obstetrics and Gynecology, vol. 38, No. 4 (Dec. 1995) 675–687.

Lyrenäs, S. et al., "Pharmacokinetics of terbutaline during pregnancy," Eur J Clin Pharmacol, vol. 29, No. 5 (1986) 619–623.

McCombs, J., "Update on tocolytic therapy," The Annals of Pharmacotherapy, vol. 29, No. 5 (May 1995) 515–522.

Miles, R.A. et al., "Pharmacokinetics and endometerial tissue levels of progesterone after administration by intramuscular and vaginal routes: a comparative study," Fertility and Sterility, vol. 62, No. 3 (Sep. 1994) 485–490.

Morgan, D.J., "Clinical pharmacokinetics of β–agonists," Clinical Pharmacokinetics, vol. 18, No. 4 (Apr. 1990) 270–294.

Nyberg, L., "Pharmacokinetic parameters of terbutaline in healthy man. An overview," Eur J Resp Dis vol. 65 Suppl. 134 (1984) 149–160.

Park, H. et al., "Physico–chemical properties of water insoluble polymers important to mucin/epithelial adhesion," Journal of Controlled Release, vol. 2 (1985) 47–57.

Ripe, E. et al., "Oral administration of terbutaline in asthmatic patients," Eur J Resp Dis, vol. 65, Suppl. 134 (1984) 171–179.

Robinson, J.R. et al., "Mechanisms of adhesion of swelling insoluble polymers to mucin–epithelial surfaces," Proceed. Intern. Symp. Control. Rel. Bioact. Mater., Geneva, Switzerland (Jul. 8–12, 1985), 32.

(List continued on next page.)

*Primary Examiner*—Carlos A. Azpuru
*Attorney, Agent, or Firm*—Lyon & Lyon LLP

[57] ABSTRACT

The present invention teaches a composition comprising a β-adrenergic agonist in a bioadhesive carrier. Preferably, the composition comprises terbutaline in polycarbophil. The present invention additionally teaches the local administration of a β-adrenergic agonist for the purpose of treating or preventing dysmenorrhea or premature labor. Using this composition and the method of treatment provides sufficient local levels of the drug to provide therapeutic efficacy, but avoids many untoward adverse events.

15 Claims, 7 Drawing Sheets

OTHER PUBLICATIONS

Robinson, J.C. et al., "Dysmenorrhea and use of oral contraceptives in adolescent women attending a family planning clinic," Am J Obstet Gynecol, vol. 166, No. 2 (Feb. 1992), 578–583.

Salamanca, A. et al., "Subendometrial contractility in menstrual phase visualized by transvaginal sonography in patients with endometriosis," Fertility and Sterility, vol. 64, No. 1 (Jul. 1995) 193–195.

Lalos, O. et al., "Effect of salbutamol on the non–pregnant human uterus in vivo," Acta Obstet Gynecol Scand, vol. 60, No. 4 (1981), 349–352.

Lockwood, C.J., "The diagnosis of preterm labor and the prediction of preterm delivery," Clinical Obstetrics ad Gynecology, vol. 38, No. 4 (Dec. 1995) 675–687.

Lyrenäs, S. et al., "Pharmacokinetics of terbutaline during pregnancy," Eur J Clin Pharmacol, vol. 29, No. 5 (1986) 619–623.

McCombs, J., "Update on tocolytic therapy," The Annals of Pharmacotherapy, vol. 29, No. 5 (May 1995) 515–522.

Miles, R.A. et al., "Pharmacokinetics and endometerial tissue levels of progesterone after administration by intramuscular and vaginal routes: a comparative study," Fertility and Sterility, vol. 62, No. 3 (Sep. 1994) 485–490.

Morgan, D.J., "Clinical pharmacokinetics of β–agonists," Clinical Pharmacokinetics, vol. 18, No. 4 (Apr. 1990) 270–294.

Nyberg, L., "Pharmacokinetic parameters of terbutaline in healthy man. An overview," Eur J Resp Dis vol. 65 Suppl. 134 (1984) 149–160.

Park, H. et al., "Physico–chemical properties of water insoluble polymers important to mucin/epithelial adhesion," Journal of Controlled Release, vol. 2 (1985) 47–57.

Ripe, E. et al., "Oral administration of terbutaline in asthmatic patients," Eur J Resp Dis, vol. 65, Suppl. 134 (1984) 171–179.

Robinson, J.R., et al., "Mechanisms of adhesion of swelling insoluble polymers to mucin–epithelial surfaces," Proceed. Intern. Symp. Control. Rel. Bioact. Mater., Geneva, Switzerland (Jul. 8–12, 1985), 32.

Robinson, J.C. et al., "Dysmenorrhea and use of oral contraceptives in adolescent women attending a family planning clinic," Am J Obstet Gynecol, vol. 166, No. 2 (Feb. 1992), 578–583.

Salamanca, A. et al., "Subendometrial contractility in menstrual phase visualized by transvaginal sonography in patients with endometriosis," Fertility and Sterility, vol. 64, No. 1 (Jul. 1995) 193–195.

Van den Berg, W. et al., "The effects of oral and subcutaneous administration of terbutaline in asthmatic patients," Eur J Resp Dis, vol. 65 Suppl. 134 (1984) 181–193.

Forman, A. et al., "Aspects of inhibition of myometrial hyperactivity in primary dysmenorrhea," Acta Obstet Gynecol Scand Suppl 113 (1983) 71–76.

Fuchs, F. et al., "Principles of tocolysis: an overview, "Preterm Birth, 2d Ed., McGraw–Hill, Inc. (1993) 217–227.

Hadfield, R. et al., "Delay in the diagnosis of endometriosis: a survey of women from the USA and the UK," Human Reproduction, vol. 11, No. 4 (1996), 878–880.

Hankins, G.D.V. et al., "A comparison of the relative toxicities of β–sympathomimetic tocolytic agents," Am J Perinatology, vol. 2, No. 4 (Oct. 1985) 338–346.

Hansen, M.K. et al., "Beta–receptor stimulation in essential dysmenorrhea," Am J Obstet Gynecol, vol. 121, No. 4 (Feb. 15, 1975) 566–567.

Harlow, S.B., "A longitudinal study of risk factors in the occurrence, duration and severity of menstrual cramps in a cohort of college women," British Journal of Obstetrics and Gynaecology, vol. 103 (Nov. 1996) 1134–1142.

Hörnblad, Y. et al., "The metabolism and clinical activity of terbutaline and its prodrug ibuterol," Europ. J. Clin. Pharmacol., vol. 10, No. 1 (1976) 9–18.

Hunter, R.H.F. et al., "Regulation of oviduct function in pigs by local transfer of ovarian steroids and prostaglandins: a mechanism to influence sperm transport," Europ. J. Obstet. Gynec. Reprod. Biol., vol. 14 (1983) 225–232.

Klein, J. et al., "Epidemiology of adolescent dysmenorrhea," Pediatrics, vol. 58, No. 5 (Nov. 1981) 661–664.

Kopelman, J.N. et al., "Randomized comparison of oral terbutaline and ritrodine for preventing recurrent preterm labor," J. Reproductive Medicine, vol. 34, No. 3 (Mar. 1989) 225–230.

Kryzmowski, T. et al., "Uterine and ovarian countercurrent pathways in the control of ovarian function in the pig," J. Reprod. Fert., Suppl. 40 (1990) 179–191.

Kullander, S. et al., "On resorption and the effects of vaginally administered terbutaline in women with premature labor," Acta Obstet Gynecol Scand, vol. 64, No. 7 (1985), 613–616.

Kullander, S. et al., "Terbutaline inhalation for alleviation of severe pain in essential dysmenorrhea," Acta Obstet Gynecol Scand, vol. 60, No. 4 (1981), 425–427.

Bulletti, C. et al., "Extracorporeal perfusion of the human uterus," Am J Obstet Gynecol, vol. 154, No. 3, Mar. 1986, 683–688.

Bulletti, C. et al., "A 48–hour preservation of an isolated human uterus: endometrial responses to sex steroids," Fertility and Sterility, vol. 47, No. 1 (Jan. 1987) 122–129.

The Canadian Preterm Labor Investigators Group, "Treatment of preterm labor with the beta–adrenergic agonist ritodrine," The New England Journal of Medicine, vol. 327, No. 5 (Jul. 30, 1992) 308–312.

Caritis, S. et al., "Effects of terbutaline on the pregnant baboon and fetus," Obstetrics and Gynecology, vol. 50, No. 1 (Jul. 1977) 56–60.

Caritis, S. et al. "Effects of terbutaline on cardiovascular state and uterine blood flow in pregnant ewes," Obstetrics and Gynecology, vol. 50, No. 5 (Nov. 1977) 603–606.

Caritis, S. et al., "A double–blind study comparing ritodrine and terbutaline in the treatment of preterm labor," Am J Obstet Gynecol, vol. 150, No. 1 (Sep. 1, 1984) 7–14.

Casanas–Roux, F. et al., "Morphometric, immunohistological and three–dimensional evaluation of the endometrium of menopausal women treated by oestrogen and Crinone, a new slow–release vaginal progesterone," Human Reproduction, vol. 11, No. 2 (Feb. 1996) 357–363.

Creasy, R.K. et al., "Basic research and clinical experience with β–adrenergic tocolytics n the United States," Preterm Birth, 2d Ed., McGraw–Hill, Inc. (1993) 243–277.

de Ziegler, D. et al., "Transvaginal administration of progesterone: the vaginal paradox and the first uterine pass effect hypothesis," Refrences en Gynécologie Obstétrique, vol. 3, No. 3 (1995) 267–272.

Einer–Jensen, N., "Counter current transfer between blood vessels in the ovarian adnex," Summary of Doctoral Thesis, Acta Obstet Gynecol Scand (1992) vol. 71: 566–567.

Einer–Jensen, N. et al., "Rapid absorption and local redistribution of progesterone after vaginal application in gilts," Acta Vet Scand (1993) vol. 34, 1–7.

Physician's Desk Reference, 50 Ed., pp. 1502–1503 (1996).

M. Åkerlund et al., "Relief of pain in primary dysmenorrhoea by β–adrenoceptor stimulating drugs" [Letter to the Editor], Acta Obstet Gynecol Scand 56:255–256 (1977).

M. Åkerlund et al., "Effects of Terbutaline on Myometrial Activity, Uterine Blood Flow, and Lower Abdominal Pain in Women with Primary Dysmenorrhoea," British Journal of Obstetrics and Gynaecology (Sep. 1976) 674–678.

M. Åkerlund et al., "Effects of Terbutaline on Human Myometrial Activity and Endometrial Blood Flow," Obstetrics and Gynecology, vol. 47, No. 5 (May 1976) 529–535.

Andersch, B. et al., "An epidemiologic study of young women with dysmenorrhea," Am J Obstet Gynecol, vol. 144, No. 6, Nov. 15, 1982, 655–660.

Bengtsson, B., "Plasma concentration and side–effects of terbutaline," Eur J Resp Dis (1984) 65, Suppl 134, 231–235.

Berg, G. et al., "Terbutaline in the treatment of preterm labour," Eur J Resp Dis (1984) 65, Suppl. 134, 219–230.

Bergman, B. et al. "Transfer of terbuatline across the human placenta in late pregnancy," Eur J Resp Dis (1984) 65, Suppl 134, 81–86.

Boyle, J., "Beta–Adrenergic Agonists," Clinical Obstetrics and Gynecology, vol. 38, No. 4 (Dec. 1995) 688–696.

Bulletti, C., et al., "Targeted drug delivery in gynaecology: the first uterine pass effect," Human Reproduction, vol. 12, No. 5 (May 1997) 1073–1079.

Bulletti, C., et al., "Extraction of estrogens by human perfused uterus," Am J Obstet Gynecol, vol. 159, No. 2 (Aug. 1988) 509–515.

Abstract, *Derwent Publications Ltd.,* AN 84–071329 ç 12!, XP002096704, AB J59 025320, Feb. 9, 1984.

PHARMACEUTICAL COMPOSITION FOR TREATING DYSMENORRHEA AND PREMATURE LABOR

This application claims the benefit of U.S. Provisional Application No. 60/058,789, filed Sep. 12, 1997, which is incorporated herein by reference.

FIELD OF THE INVENTION

The invention relates to a pharmaceutical composition and the local administration thereof for the purpose of treating or preventing dysmenorrhea or premature labor.

BACKGROUND OF THE INVENTION

Both dysmenorrhea and premature labor affect significant numbers of American women; however, treatment regimens are still lacking for both conditions. Dysmenorrhea, menstrual cramps, affects on average over 50% of women and results in frequent absenteeism or loss of activity. Andersch, B., Milsom I., *An Epidemiologic study of young women with dysmenorrhea, A.J.O.G.,* 144:655–60 (1982). Young women report a somewhat higher incidence of dysmenorrhea than the average, with estimates ranging from 67% to 72%. Harlow, S. D., Parck M., *A longitudinal study of risk factors for the occurrence, duration and severity of menstrual cramps in a cohort of college women, Br. J. Obstet. Gynaecol.,* 103:1134–42 (1996). Severe pain has been reported by 7 to 15% of women. Id.

In the United States alone an estimated 140 million work and school hours are lost per year due to this condition. Klein, J. R., Litt, I. F., *Epidemiology of adolescent dysmenorrhea, Pediatrics,* 68:6661–64 (1981). About 42% of United States university students between the ages of 17 and 19 have had to be absent from their daily activities at least once due to dysmenorrhea. Id. Approximately 15% of young women have one to three days of incapacitation each month and dysmenorrhea is the leading cause of short-term school absenteeism among adolescent young women. Id. This disease, with its constant regularity, results in notable social, educational, and economic losses in this country.

Dysmenorrhea consists of painful uterine cramping and is often accompanied by associated symptoms including nausea, vomiting, diarrhea, and lower backaches. Treatments for dysmenorrhea currently focus on the use of non-steroidal antiinflammatory drugs (NSAIDs). These drugs include, for instance, naproxen, ibuprofen, mefenamic acid, and meclofenamate sodium. Oral contraceptives are also used by some women in the treatment of dysmenorrhea. Despite the fact that these two regimens can be used together, the recurring problems of dysmenorrhea have not been eliminated for many women.

Specifically, the painful uterine cramping associated with dysmenorrhea is probably triggered by vasopressin and increased production of prostaglandins. The current method of treatment, with NSAIDs, blocks prostaglandin production and acts as a painkiller. Although this method of treatment is effective in some women and decreases symptoms in other women, researchers have wondered whether blocking the dysmenorrheic process at an earlier step would provide more effective treatment in the prevention of uterine cramping.

Although no link has formally been established, some researchers believe that untreated dysmenorrhea may play a role in the genesis of such serious clinical conditions as endometriosis. Recent studies have shown that endometriosis is associated with dyskinetic patterns of uterine contractions at the time of menses. Salamanca, A., Beltran, E., *Subendometrial Contractility in Menstrual Phase Visualized by Transvaginal Sonography in Patients with Endometriosis. Fertil. Steril.,* 65:193–95 (1995). Additionally, the symptoms of dysmenorrhea can often mask the more serious disease of endometriosis. Symptoms of dysmenorrhea often occur in women with endometriosis for nearly ten years on average prior to laproscopic diagnosis of the later disease. Hadfield, R., Mardon, H., Barlow, D., Kennedy, S., *Delay in the Diagnosis of Endometriosis: A Survey of Women from the U.S.A. and U.K. Human Reprod.,* 11:878–80 (1996).

Premature labor also affects a significant number of women in the United States. Preterm delivery is defined as delivery prior to 30 weeks of gestation. This phenomenon complicates 8 to 10% of births in the United States and is a leading cause of neonatal morbidity and mortality. Lockwood, C. J., *The diagnosis of PTL and the prediction of preterm delivery, Clinical Obstetrics and Gynecology,* Pitkin, R. M., Scott, J. R. (eds.), 38:675–678 (1995). In fact, prematurity causes 75% of perinatal deaths in this country. McCombs, J., *Update on Tocolytic Therapy, Annals of Pharmacotherapy,* 29:515–522 (1995). Premature infants also have an increased risk of other serious conditions, including respiratory distress syndrome, hyaline membrane disease, intracranial intraventricular hemorrhage, necrotizing enterocolitis, sepsis, and have an increased incidence of cerebral palsy. Id.

Currently, preventing preterm delivery focuses on the early diagnosis of impending premature labor in women with intact membranes. Oral tocolytic agents, or uterine relaxants, are the treatment of choice. Tocolytic agents include progestational compounds, β-adrenergic agonists, NSAIDs, calcium agonists, oxytocin, or vasopressin agonists, and potassium channel openers. The most widely used of these are the β-adrenergic agonists such as terbutaline and ritodrine. It should be noted, however, that of the β-adrenergic agonists, only ritodrine is approved by the F.D.A. for use in preterm labor. Other β-adrenergic agonists, such as terbutaline, are approved for other conditions (e.g., asthma) but have been used by practitioners in the treatment of premature labor. As these drugs are given orally, however, treatment is accompanied by serious side effects. Research has failed to produce a β-adrenergic agonist that is selective for the receptors in the uterus and consequently lacking of some of the most serious adverse events.

Terbutaline is a β-adrenergic agonist. Its chemical formula is 5-[2-[(1,1-dimethylethyl)amino]-1-hydroxyethyl]-1,3-benzenediol. The empirical formula of terbutaline is $C_{12}H_{19}NO_3$. Its molecular weight is 225.29. Its structural formula is as follows:

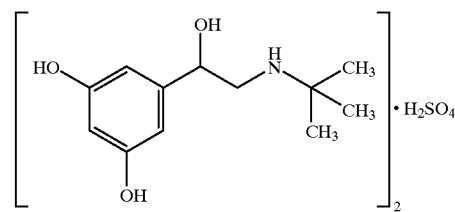

Terbutaline, as a β-adrenergic agonist, has been used primarily as a bronchodilator. β-adrenergic agonists exert their pharmacologic effects by activation of adenyl cyclase, the enzyme that catalyzes the conversion of adenosine triphosphate (ATP) to cyclic adenosine monophosphate (cAMP). Activation of adenyl cyclase by β-adrenergic agonists increases intracellular levels of cAMP. Cyclic AMP in turn reduces the availability of intracellular free $Ca^{2+}$, which is required for the activation of myosin light-chain kinase, the enzyme that phosphorylates myosin and thereby allows it to combine with actin to form actomyosin. Lack of $Ca^{2+}$ results in disruption of the actin-myosin interaction, with resultant inhibition of smooth muscle contractility. Due to their direct effects on smooth muscle contractility, β-adrenergic agonists, such as terbutaline, may prove to be an effective therapy for both dysmenorrhea and premature labor.

In fact, oral and intravenous terbutaline has been used as a reasonably effective therapy for preterm labor. Studies have shown that oral or IV therapy can stop contractions or postpone delivery. Lyrenas, S., Grahnen, A., Lindberg, B., et. al., *Pharmacokinetics of Terbutaline During Pregnancy, Eur. J. Clin. Pharmacol.*, 29:619–623 (1986); Berg., G., Lindberg, C., Ryden G., *Terbutaline in the Treatment of Preterm Labour, Eur. J. Respir. Dis.*, 65:219–230 (1984). Adverse events can present significant problems in the treatment of preterm labor with terbutaline and are discussed further below.

A few studies also document the use of terbutaline in the treatment of dysmenorrhea. In one study, treatment with IV terbutaline inhibited myometrial activity, increased blood flow to the uterus, and relieved the pain occurring during uterine contractions accompanying dysmenorrhea. Åkerlund, M., Andersson, K. E., and Ingemarsson, E., *Effects of Terbutaline on Myometrial Activity, Uterine Blood Flow, and Lower Abdominal Pain in Women with Primary Dysmenorrhoea, Br. J. of Obstet. & Gyn.*, 83(9):673–78 (1976). Terbutaline inhalers have even been evaluated for the treatment of dysmenorrhea. Kullander, S., Svanberg, L., *Terbutaline Inhalation for Alleviation of Severe Pain in Essential Dysmenorrhea, Acta Obstet. Gynecol. Scand.*, 60:425–27 (1981). This therapy did provide some efficacy; however, treatment was not sufficient for most patients, who had to supplement with other medications for adequate relief. Further, the effect of each spray lasted as little as 1 hour. Id. One other β-adrenergic agonist, salambutol, showed pain relief when administered intravenously. Lalos, O., Joelsson, I., *Effect of Salbutamol on the Non-Pregnant Human Uterus In Vivo, Acta Obstet. Gynecol. Scand.*, 60:349–52 (1981).

Several problems with administration and adverse effects, however, prevent women affected by dysmenorrhea and premature labor from being able to take full advantage of this therapy. First, β-adrenergic agonists such as terbutaline have a low bioavailability after oral administration. These pharmaceuticals are well absorbed but have extensive first-pass sulphation. Bioavailability has been estimated at between 15 and 20%. Concomitant food intake additionally decreases bioavailability by a further 30%. *Bricanyl: Scientific brochure, Astra France Laboratories* (1993).

Second, adverse effects significantly limit the current utility of terbutaline in the treatment of preterm labor and dysmenorrhea. Placental transfer of β-adrenergic agonists such as terbutaline is relatively rapid; thus, adverse effects are observed in the fetus and neonate while treating premature labor using oral administration. Morgan, D. J., *Clinical Pharmacokinetics of β-Agonists, Clin. Pharmacokin.*, 18:270–294 (1990). Thus, when treating preterm labor, adverse events can affect not only the woman but also her child.

The most serious adverse events are cardiovascular in nature. Intravenous administration of terbutaline has been associated with palpitations and peripheral tremors. Åkerlund, M., Andersson, K. F., Ingemarsson, I., *Effects of Terbutaline on Myometrial Activity, Uterine Blood Flow and Lower Abdominal Pain in Women With Primary Dysmenorrhea. Br. J. Obstet. Gyncol.*, 83:673–78 (1976). As a sympathomimetic amine, terbutaline can cause problems in patients with cardiovascular disorders (including arrhythmia, coronary insufficiency and hypertension), as well as with patients with hyperthyroidism, diabetes mellitus, or a history of seizures. Significant adverse reactions have been reported following administration of terbutaline to women in labor including pulmonary edema and hypoglycemia in the mother and or neonate child. Intravenous terbutaline has also been reported to aggravate preexisting diabetes and ketoacidosis. Other adverse events include: tremors, nervousness, increased heart rate, palpitations, and dizziness. Less frequent adverse effects include headaches, drowsiness, vomiting, nausea, sweating, muscle cramps, and ECG changes.

These adverse effects have precluded the use of β-agonists such as terbutaline to prevent or treat dysmenorrhea as it considered to be a benign or non-threatening condition. Akerlund, M., Andersson, K. E., and Ingemarsson, E., *Effects of Terbutaline on Myometrial Activity, Uterine Blood Flow, and Lower Abdominal Pain in Women with Primary Dysmenorrhoea, Br. J. of Obstet. & Gyn.*, 83(9):673–78 (1976). Further, the risks involved have limited the use of these pharmaceutical agents in the treatment of preterm delivery and premature labor as the benefits must be balanced carefully against the seriousness of the adverse events involved.

In an attempt to address the severity of the adverse events involved, researchers have been attempting to identify another effective means for administering the drug that would decrease the risk involved. It is known that terbutaline can be administered directly to the uterus, resulting in preferential local concentrations as compared to peripheral circulation concentrations. Kullander et al. studied the correlation between the uterine and blood concentrations of terbutaline after insertion of a terbutaline-impregnated polymer ring (10% terbutaline sulfate in a 5 g vaginal ring), terbutaline in a cellulose gel (0.1 mg in 1 mL cellulose gel), or a placebo ring in a patient 24 hours before hysterectomy. Kullander, S., Svanberg, L., *On resorption and the effect of vaginally administered terbutaline in women with premature labor. Acta. Obstet. Gynecol. Scand.*, 64:613–16 (1985). The methods followed in this reference, however, have distinct disadvantages. The water soluble cellulose-gel used can wash away and the use of a polymer ring can be uncomfortable and unpalatable for the woman, and thus both are distinctly disadvantageous.

Other pharmaceutical compounds with problematic adverse events have been successfully administered locally. The bioadhesive carrier of the present invention has been used in other drug delivery systems, although with different results than in the present invention. For example, polycarbophil is a main ingredient in the vaginal moisturizer Replens®. It has also been used as a base for compositions with other active substances such as progesterone (Crinone®) (see U.S. Pat. No. 5,543,150) and Nonoxynol-9 (Advantage-S) (see U.S. Pat. No. 5,667,492).

Additionally, it is important that pharmaceutical compositions do not interfere with all contractions and the homeostasis of menstruation. As menstrual blood does not clot, normal, regularized contractions are helpful to stop the bleeding. If there are no contractions, then the patient may not stop bleeding and may hemorrhage. Thus, it is an object of the invention to interfere with the dyskinetic contractions causing dysmenorrhea, without stopping contractions entirely.

SUMMARY OF THE INVENTION

The present invention relates to a pharmaceutical composition comprising a therapeutically effective amount of a β-adrenergic agonist together with a pharmaceutically acceptable bioadhesive carrier and the local administration of a β-adrenergic agonist for the purpose of treating or preventing dysmenorrhea or premature labor. Using this composition and the method of treatment provides sufficient local levels of the drug to provide therapeutic efficacy, but avoids many untoward adverse events.

DETAILED DESCRIPTION OF THE INVENTION

Figure 1:
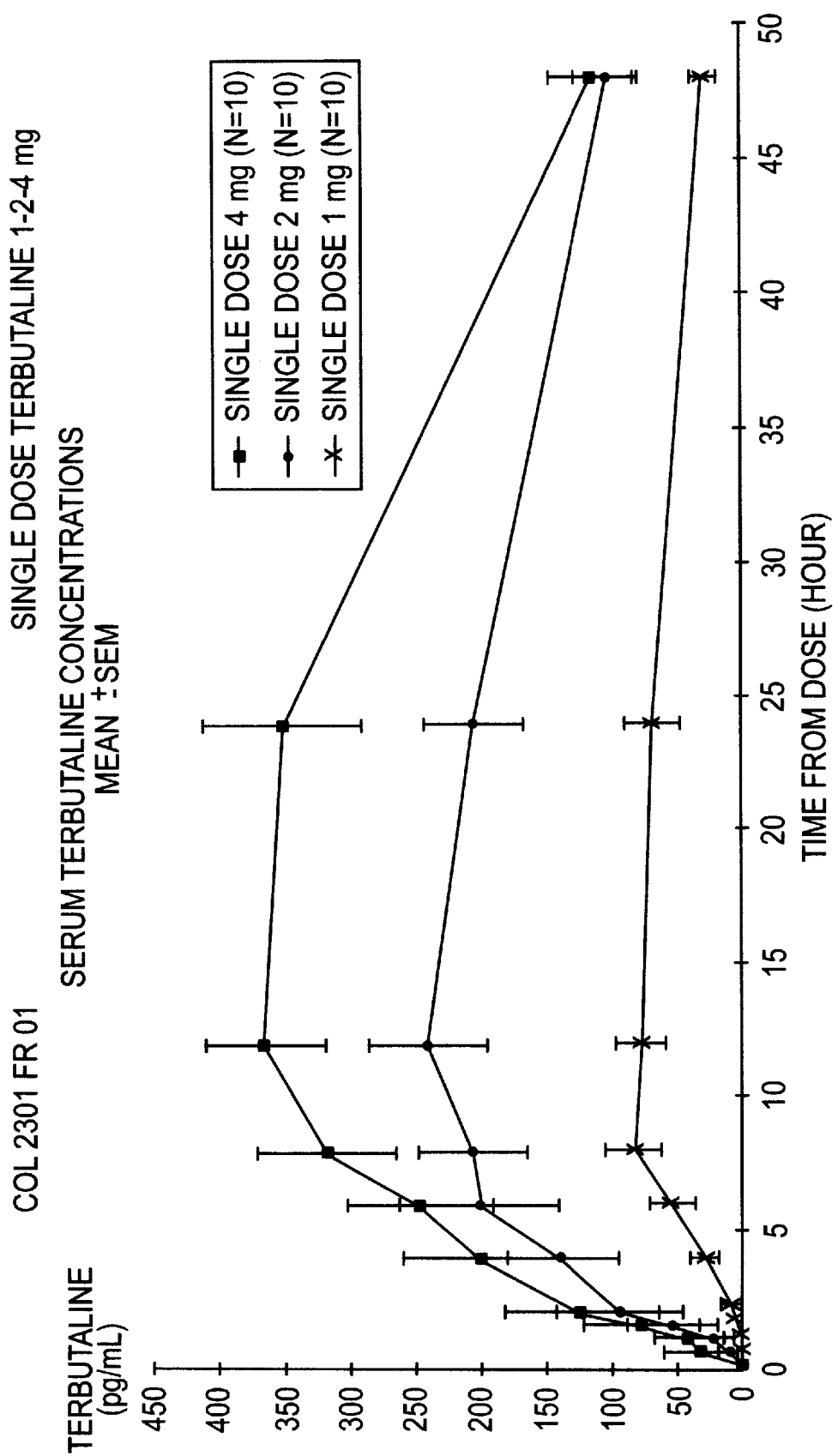
FIG. 1 illustrates the serum terbutaline levels in a single dose study. Doses were 4 mg, 2 mg, and 1 mg. The terbutaline gel was administered transvaginally once.

The present invention is related to a composition comprising therapeutically effective amount of a β-adrenergic agonist together with a pharmaceutically acceptable bioadhesive carrier. Preferably terbutaline is used as the β-adrenergic agonist. The present invention preferably comprises a $β_2$ specific adrenergic agonist. Other acceptable β-adrenergic agonists include ritodrine, isoxsuprine, fenoterol, salambutol, hexoprenaline, metaproterenol, bitolterol and pirbuterol. The invention comprises a uterine smooth muscle relaxant for both pregnant and non-pregnant women and has been specifically designed for vaginal administration. The bioadhesive carrier, which may be in a gel formulation, contains a polycarbophil base designed to give controlled and prolonged release of terbutaline, or another β-adrenergic agonist, through the vaginal mucosa. This route of administration avoids first-pass metabolism problems. The direct delivery to the uterus allows for lower systemic drug concentrations. These two properties help avoid many significant adverse events.

The present invention is additionally related to a method of preventing or treating dysmenorrhea comprising administering the composition vaginally. Additionally, the present invention includes a method of preventing or treating premature labor comprising administering the composition vaginally. Most preferably, in preventing or treating both conditions, 1 to 1.5 g of the composition is administered; although, acceptable amounts of the composition to be administered include 0.5 to 2.5 g. The composition administered can contain between 1 to less than about 8 mg of terbutaline per dose, preferably containing 1 to 4 mg, and most preferably containing 2 to 4 mg. Dosages of 8 or more mg are not recommended, however, because side effects may be noted in some individuals at such levels. The composition can be administered every 12 to 48 hours, but is preferably administered every 24 hours. The composition can be administered during dysmenorrhea or optionally including one or more days prior to the anticipated onset of dysmenorrhea. Similarly, the composition may be administered during premature labor or to prevent the onset of anticipated premature labor.

The present invention comprises a dosing regimen and manner of treating dysmenorrhea. In practicing the invention, a patient need not wait until the onset of menses and the occurrence of pain to begin treatment. The present invention comprises administration of the composition as soon as the patient realizes that she is nearing the onset of menses, for example within a day or two. This method of administration is based on pharmacokinetic data below, and prevents the process of dyskinetic contractions from occurring, rather than treating them once the contractions have already begun.

Another important aspect of the invention is that the uterorelaxant formulation can correct dysmenorrhea and its dyskinetic contractions, without interfering with the normal contractions and bleeding during menstruation. Dysmenorrhea appears to involve dyskinetic contractions, which are erratic and abnormal. This is in contrast to other theories of dysmenorrhea as comprises solely an increase in the amplitude and frequency of contraction. The inventors believe that in dysmenorrhea the nature of contractions change so that there are not only antegrade contractions (fundus to cervix), but also retrograde contractions (cervix to fundus), and non-functional fibrillations. The composite of the present invention appears to provide relief by way of a selective action on the dyskinetic contractions without preventing the normal, regularized contractions necessary for menstruation.

The specific drug delivery formulation chosen and used in the examples below comprises a cross-linked polycarboxylic acid polymer formulation, generally described in U.S. Pat. No. 4,615,697 to Robinson (hereinafter "the '697 patent"), which is incorporated herein by reference. In general, at least about eighty percent of the monomers of the polymer in such a formulation should contain at least one carboxyl functionality. The cross-linking agent should be present at such an amount as to provide enough bioadhesion to allow the system to remain attached to the target epithelial surfaces for a sufficient time to allow the desired dosing to take place.

For vaginal administration, such as in the examples below, preferably the formulation remains attached to the epithelial surfaces for a period of at least about twenty-four to forty-eight hours. Such results may be measured clinically over various periods of time, by testing samples from the vagina for pH reduction due to the continued presence of the polymer. This preferred level of bioadhesion is usually attained when the cross-linking agent is present at about 0.1 to 6.0 weight percent of the polymer, with about 1.0 to 2.0 weight percent being most preferred, as long as the appropriate level of bioadhesion results. Bioadhesion can also be measured by commercially available surface tensiometers utilized to measure adhesive strength.

The polymer formulation can be adjusted to control the release rate of the β-adrenergic agonist, such as terbutaline, by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

A preferred polymer for use in such a formulation is Polycarbophil, U.S.P., which is commercially available from B.F. Goodrich Speciality Polymers of Cleveland, Ohio under the trade name NOVEON®-M1. The United States Pharmacopeia, 1995 edition, United States Pharmacopeial Convention, Inc., Rockville, Md., at pages 1240–41, indicates that polycarbophil is a polyacrylic acid, cross-linked with divinyl glycol.

Other useful bioadhesive polymers that may be used in such a drug delivery system formulation are mentioned in the '697 patent. For example, these include polyacrylic acid polymers cross-linked with, for example, 3,4-dihydroxy-1, 5-hexadiene, and polymethacrylic acid polymers cross-linked with, for example, divinyl benzene.

Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

The bioadhesive formulation may be in the form of a gel, cream, tablet, pill, capsule, suppository, film, or any other pharmaceutically acceptable form that adheres to the mucosa and does not wash away easily. Different formulations are further described in the '697 Patent, which is incorporated herein by reference.

Additionally, the additives taught in the '697 patent may be mixed in with the cross-linked polymer in the formulation for maximum or desired efficacy of the delivery system or for the comfort of the patient. Such additives include, for example, lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

The specific preparation (COL-2301) used in the studies discussed in the examples consists of the following ingredients.

TABLE 1

Preferred Compositions

| Active Ingredient mg/g | 1.0 | 2.0 | 4.0 |
| --- | --- | --- | --- |
| Terbutaline (sulfate) % (w/w) | 0.1% | 0.2% | 0.4% |
| Purified Water | 755.4 | 754.4 | 752.4 |
| Glycerin | 139.0 | 139.0 | 139.0 |
| Light liquid paraffin | 42.0 | 42.0 | 42.0 |
| Carbomer 934P | 30.0 | 30.0 | 30.0 |
| Polycarbophil | 20.0 | 20.0 | 20.0 |
| Methylparaben | 1.8 | 1.8 | 1.8 |
| Sorbic acid | 0.8 | 0.8 | 0.8 |
| Sodium Hydroxide | 0.0–2.0 | 0.0–2.0 | 0.0–2.0 |
| LABRAFIL ® M2130 | 10 | 10 | 10 |

Sorbic acid is a preservative, which may be substituted by any other approved preservative, such as benzoic acid or propionic acid.

Carbomer is a gel former, preferably Carbopol 934P, but may be substituted by other gel formers including, but not limited to, Carbomer 974P, Carbomer 980, methyl cellulose or propyl cellulose.

LABRAFIL® M2130 is a lubricant/whitening agent to provide lubricity and add color to the gel; alternatives may be used, and coloring may be left out altogether.

Glycerin is a humectant; alternative humectants include, for example, propylene glycol or dipropylene glycol.

Preparation of the formulation involves hydration of the polymers, separate mixing of water-soluble ingredients (the "polymer phase") and oil-soluble ingredients (the "oil phase"), heating and mixing of the two phases, and homogenization of the mixture. All ingredients in COL-2301 are well known and readily available from suppliers known in the industry.

The polymer phase may generally be prepared by mixing the water (with about 3% excess volume of water to account for evaporative losses), sorbic acid, and methylparaben together. This mixture is heated to 75° C. The solution is cooled, generally to room temperature, and then the polycarbophil and Carbomer are added. The polymers are hydrated by mixing for several hours, generally about 2–3 hours until a uniform, smooth, homogenous, lump-free gel-like polymer mixture is obtained. When the polymers are completely hydrated, the terbutaline is added and mixed in, until a homogeneous suspension is obtained.

The oil phase is generally prepared by melting together the LABRAFIL® M2130, glycerin, and light liquid paraffin, by heating to 75 to 78° C. The mixture is cooled to about 60° C., while the polymer phase is warmed to about the same temperature. The polymer phase is then added to the heated oil phase. The two phases are mixed thoroughly, producing a uniform, creamy white product. Sodium hydroxide is added, as needed, to produce a pH of about 2.5–4.5, generally about 4. When the mixture has cooled, it is de-aerated.

As will be apparent to those skilled in the art, the composition of the formulation can be varied to affect certain properties of the formulation. For example, the concentration of the bioadhesive polymer can be adjusted to provide greater or lesser bioadhesion. The viscosity can be varied by varying the pH or by changing the concentration of the polymer or gel former. The relative concentrations of the oils compared to the water can be varied to modulate the release rate of the terbutaline from the drug delivery system. The pH can also be varied as appropriate or to affect the release rate or bioadhesiveness of the formulation.

One of the surprising, but important aspects of the present formulation is that it allows the drug to be administered effectively even during menses. The particular bioadhesive qualities prevent the composition from being diluted or washed away, as would be expected with other bioadhesive preparations. This characteristic increases the utility of the present formulation.

Additionally, in light of the information disclosed in U.S. Pat. No. 5,543,150, it now appears that this bioadhesive formulation can provide local vaginal administration of different drugs to yield significant local drug levels while maintaining serum levels low enough to avoid most undesired side effects. It was a surprising result that this formulation serves as an acceptable carrier for two different active ingredients—progesterone, and now terbutaline. Now, given its demonstrated flexibility and range of efficacy, it is reasonable to expect that the bioadhesive formulation will work with other active ingredients as well. EXAMPLES Example 1

The Pharmacokinetic Parameters of the Terbutaline Composition, A Single Dose Study The objective of this study was to assess the pharmacokinetic parameters of the terbutaline and polycarbophil composition following a single dose regimen comparing progressively increasing concentrations. This open-label study was conducted in ten healthy female volunteers with a mean age of 25±SD (Standard Deviation) of 3.93 years. This study consisted of a 30 day screening period and a 24 hour treatment period with a follow-up evaluation conducted two days after administration of the final dose. The drug was administered transvaginally at 9:00 a.m. A wash out period of at least one week as observed between each of the four doses of the drug. All subjects were given an estro-progestative pill, to ensure that all study participants were at the same point in their menstrual cycle. They began dosing on day 7 to 10 of their pill intake for the single dose study. Serum terbutaline concentrations were obtained from blood samples collected predosing on the mornings of treatment, at frequent intervals during the initial 24 hours post dose (0.5, 1, 1.5, 2, 4, 6, 8, 12, 24 hours) and at 48 hours post dose. Serum terbutaline concentrations were determined using gas chromatography-mass spectrometry. Pharmacokinetic parameters were computed using concentration-time data for each subject following intake of the last dose of investigational drug on the morning of study day 6. The following pharmacokinetic parameters were computed: area under the drug concentration-time curve from time 0 to time t ($AUC_{0-t}$), where t is the time of the last measurable concentration; peak drug concentration ($C_{max}$); time to peak drug concentration ($t_{max}$); steady state drug concentration ($C_{ss}$); and, elimination half-life ($t_{1/2}$).

All ten subjects completed the study for the 0.1%, 0.2%, and 0.4% (w/w) concentrations. For each dose, the onset of serum terbutaline concentrations occurred within 1 to 2 hours. (See FIG. 1 and Table 2 showing terbutaline concentrations for each tested dose). Terbutaline concentrations increased slowly reaching $C_{max}$ after 13–14 hours and thereafter remained flat (steady state) for 24 hours with a mean steady state concentration ($C_{ss}$) of approximately 300 pg/mL with the 0.4% concentration. Concentrations were still detectable for up to 48 hours (mean±SEM (Standard Error of the Mean) of 113.11±32.25 pg/mL for the 0.4% concentration). Terbutaline absorption exhibited dose-dependent pharmacokinetics as reflected by the increase in $AUC_{0-48}$ values (see Table 2 and FIG. 1) to increases in terbutaline dosing. Mean $t_{1/2}$ estimates varied from 18 to 29 hours according to the dose administered and markedly exceeded measured $t_{1/12}$ after terbutaline administration by intravenous or subcutaneous routes, as had been found in the prior art.

TABLE 2

Single Dose Study, Pharmacokinetic Parameters

| Single Dose Study | | Pharmacokinetic Parameters (mean ± SEM) | | | |
|---|---|---|---|---|---|
| Terbutaline Dose | n | $C_{max}$ (pg/mL) | $T_{max}$ (h) | $C_{ss}$ (pg/mL) | $t_½$ (h) | $AUC_{0\ to\ 48}$ (pg.h/mL) |
| 0.1% | 10 | 117 ± 59 | 13 ± 6 | 56 ± 41 | 18 ± 12 | 2281 ± 1836 |
| 0.2% | 10 | 297 ± 170 | 13 ± 6 | 191 ± 108 | 29 ± 15 | 8011 ± 4699 |
| 0.4% | 10 | 479 ± 149 | 14 ± 7 | 294 ± 115 | 24 ± 16 | 11893 ± 5277 |

Example 2

The Pharmacokinetic Parameters of the Terbutaline Composition, A Multiple Dose Study The multiple dose study was an open-label study conducted in 12 healthy female volunteers with a mean age±SD of 25±4.13 years. The dose used in this study was 0.4%. This study consisted of a 30 day screening period, a 6 day treatment period, and a 2 day follow-up. The drug was administered transvaginally once daily at 9:00 a.m. All subjects were given an estro-progestative pill, to ensure that all study participants were at the same place in their menstrual cycle. They began dosing on day 13 to 16 of their pill intake for the multiple dose study. Serum terbutaline concentrations were obtained from blood samples collected predosing on the mornings of treatment, at frequent intervals during the initial 24 hours post-dose (0.5, 1, 1.5, 2, 4, 6, 8, 12, and 24 hours), and at 48 hours post-dose. Samples were also obtained just before each administration and at regular intervals after the last dose (0.5, 1, 1.5, 2, 4, 6, 8, 12, and 24 hours). Serum terbutaline concentrations were determined using gas chromatography-mass spectrometry.

Figure 2:
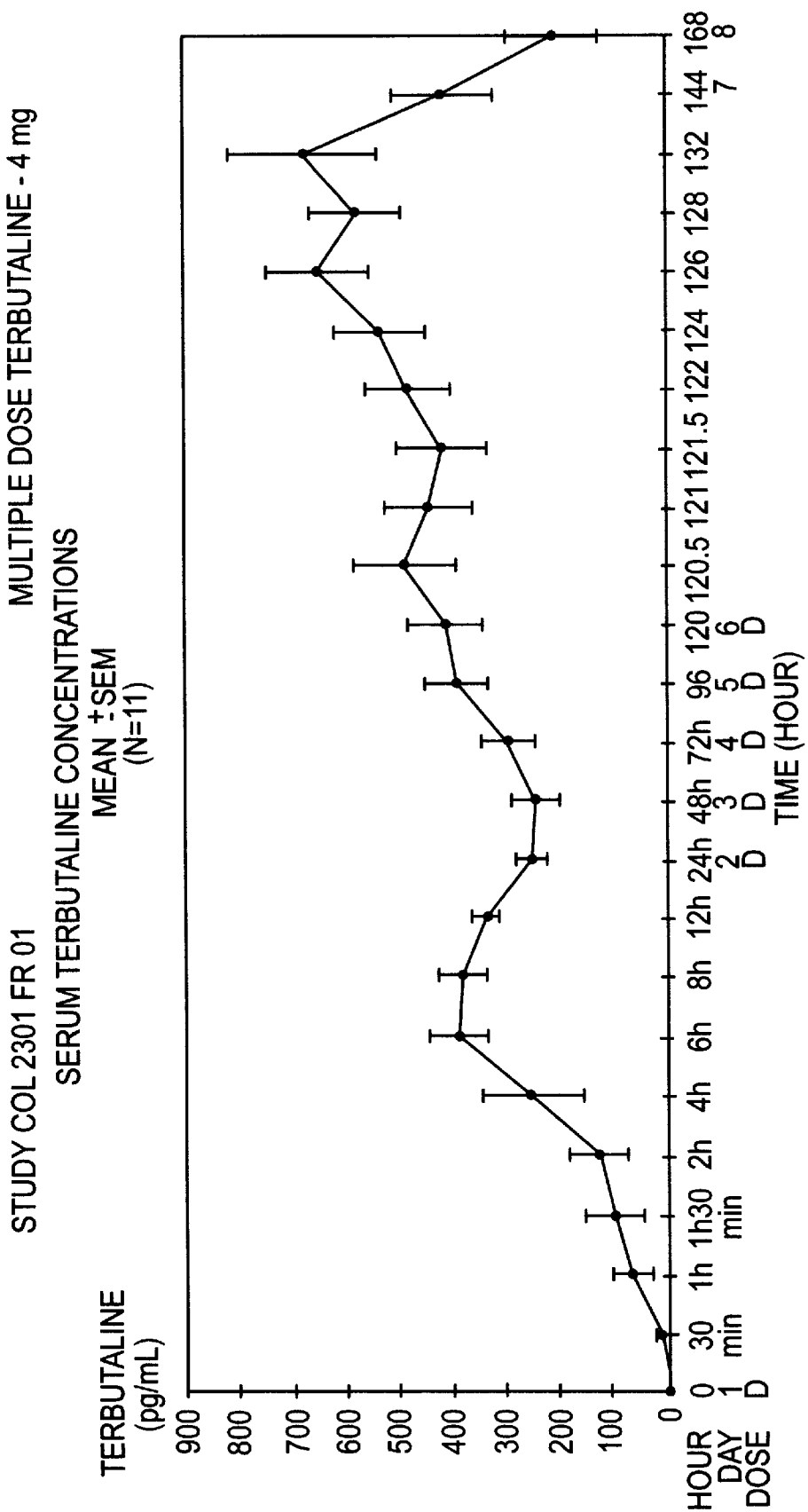
FIG. 2 illustrates the serum terbutaline levels in a multiple dose study. Doses were 4 mg, 2 mg, and 1 mg. The terbutaline gel was administered transvaginally once daily for six days.

Pharmacokinetic parameters were computed using concentration-time data for each subject following intake of the last dose of investigational drug on the morning of study day 6. The following pharmacokinetic parameters were computed: area under the drug concentration-time curve from time 0 to time t ($AU_{0-t}$), where t is the time of the last measurable concentration; peak drug concentration ($C_{max}$); time to peak drug concentration ($t_{max}$); steady state drug concentration ($C_{ss}$); and, elimination half life ($t_{1/2}$). Eleven subjects completed the study, with one subject withdrawing from the study due to lipothymia occurring just before first dose administration and recurring 30 minutes after the first dose. Pharmacokinetic parameters are presented in FIG. 2 and Table 3. $C_{max}$ was reached after approximately 9 hours (477±259 pg/mL) on day 1 and was multiplied by approximately two-fold on day 6. Moreover, it remained well below the known threshold susceptible to trigger systemic adverse events such as tachycardia and tremor, the latter reported as being approximately 3,000–3,500 pg/mL. Terbutaline steady state concentration was achieved after the first dose (mean±SEM: 287±96 pg/mL). The mean $C_{ss}$ was 10 to 15 times less than therapeutic concentrations of terbutaline for intravenous preterm labor therapy described in the prior art. See Lyrenas, S, Grahnen A, Lindberg B. et al., *Pharmacokinetics of Terbutaline During Pregnancy, Eur. J. Clin. Pharmacol.*, 29:619–23 (1986). Comparison of the $AUC_{0-24}$ for days 1 and 6 revealed a two-fold increase. Mean $t_{1/2}$ estimates were 51 hours on day 6.

TABLE 3

Multiple Dose Study, Pharmacokinetic Parameters

| Multiple Dose Study | | | Pharmacokinetic Parameters (mean ± SEM) | | | | |
|---|---|---|---|---|---|---|---|
| Terbutaline Dose | Day | n | $C_{max}$ (pg/mL) | $T_{max}$ (h) | $C_{ss}$ (pg/mL) | $t_½$ (h) | $AUC_{0\ to\ 48}$ (pg.h/mL) |
| 0.4% | 1 | 11 | 477 ± 259 | 9 ± 6 | 287 ± 96 | — | 6896 ± 2304 |
| 0.4% | 6 | 11 | 769 ± 465 | 9 ± 5 | 563 ± 339 | 51 ± 91 | 13512 ± 8135 |

Example 3:

A Dose Comparison

Both the single and multiple dose studies discussed in the preceding examples also evaluated the 0.8% w/w concentration. The average age ±SD for the single and multiple dose studies at the 0.8 dose were 26±3.42 and 26±4.12, respectively. The pharmacokinetic parameters from the study follow in Tables 4 and 5.

TABLE 4

Single Dose Study, Pharmacokinetic Parameters

| Single Dose Study | | | | | | |
|---|---|---|---|---|---|---|
| Terbut- | | Pharmacokinetic Parameters (mean ± SEM) | | | | |
| aline Dose | n | $C_{max}$ (pg/mL) | $T_{max}$ (h) | $C_{ss}$ (pg/mL) | $t_{½}$ (h) | $AUC_{0\ to\ 48}$ (pg.h/mL) |
| 0.8% | 8 | 787 ± 434 | 10 ± 3 | 579 ± 300 | 20 ± 7 | 23222 ± 13530 |

TABLE 5

Multiple Dose Study, Pharmacokinetic Parameters

| Multiple Dose Study | | | | | | | |
|---|---|---|---|---|---|---|---|
| Terbut- | | | Pharmacokinetic Parameters (mean ± SEM) | | | | |
| aline Dose | Day | n | $C_{max}$ (pg/mL) | $T_{max}$ (h) | $C_{ss}$ (pg/mL) | $t_{½}$ (h) | $AUC_{0\ to\ 48}$ (pg.h/mL) |
| 0.8% | 1 | 10 | 794 ± 394 | 11 ± 5 | 567 ± 322 | — | 13618 ± 7718 |
| 0.8% | 6 | 10 | 1537 ± 906 | 9 ± 2 | 1135 ± 679 | 19 ± 4 | 27246 ± 16299 |

Figure 3:
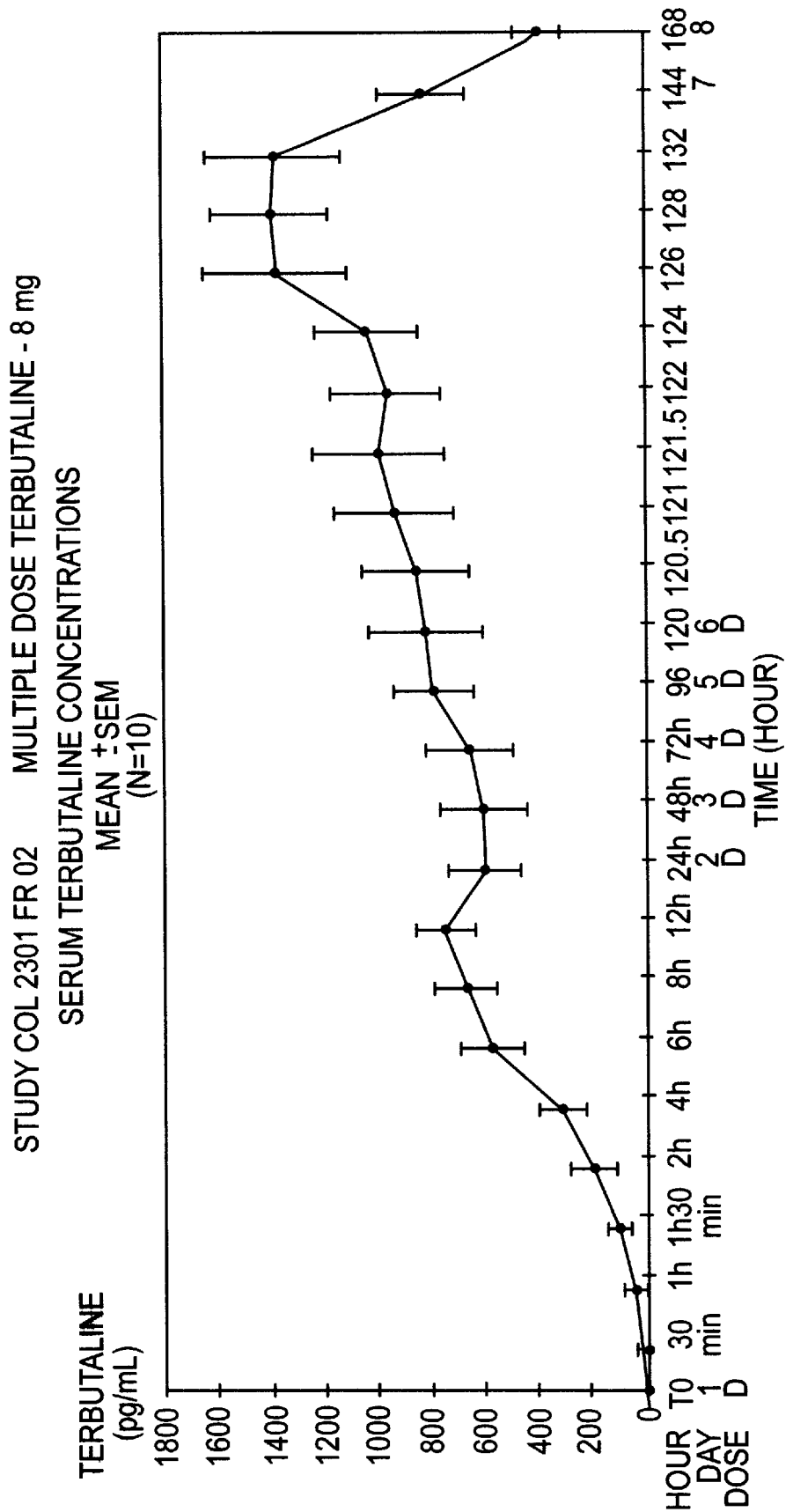
FIG. 3 illustrates the serum terbutaline levels in a single dose study. The dose given was 8 mg. The terbutaline gel was administered transvaginally once.
Figure 4:
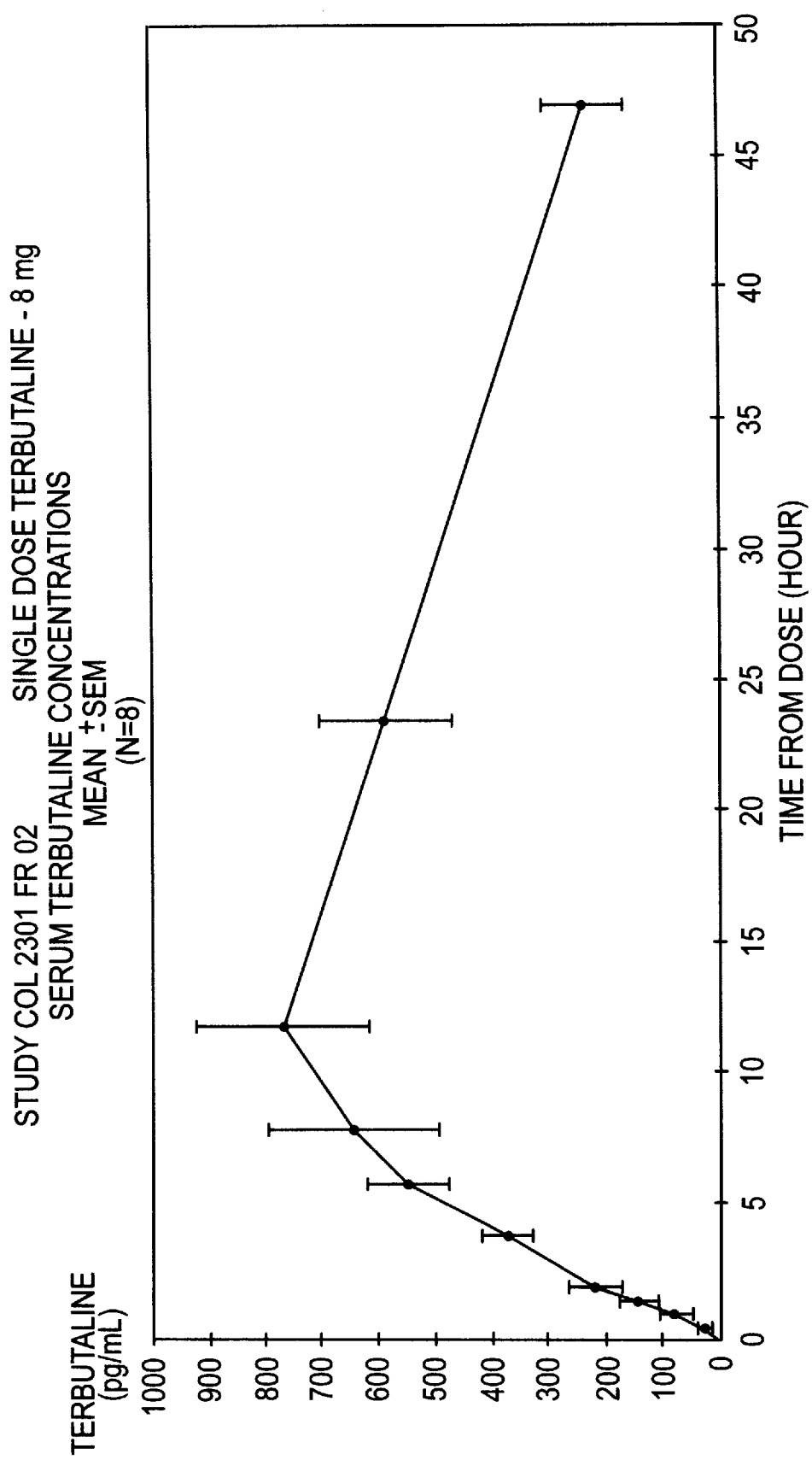
FIG. 4 illustrates the serum terbutaline levels in a multiple dose study. The dose given was 8 mg. The terbutaline gel was administered transvaginally once daily for six days.
Figure 5:
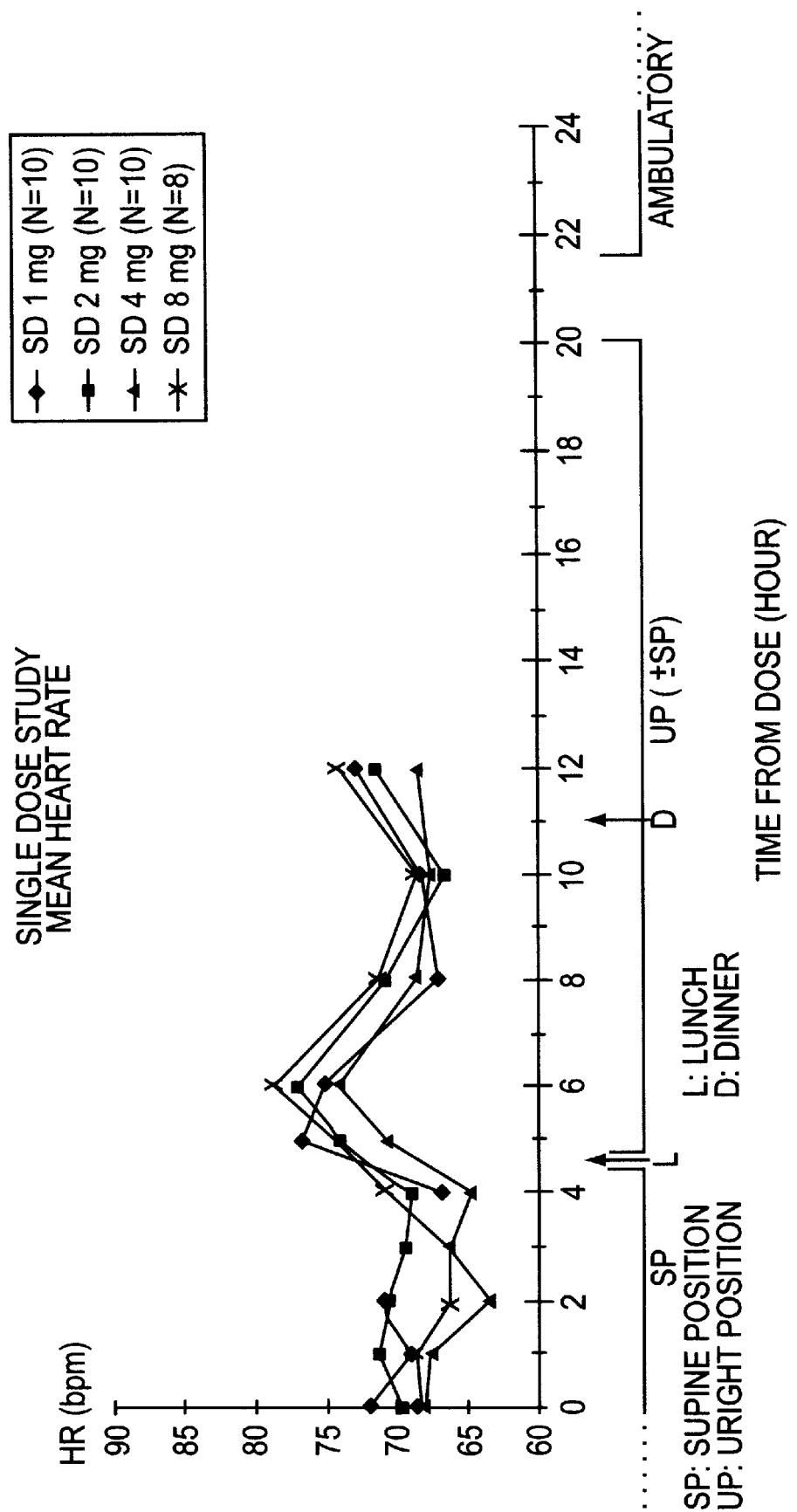
FIG. 5 illustrates mean heart rates in a single dose study. Doses were 8 mg, 4 mg, 2 mg, and 1 mg. The terbutaline gel was administered transvaginally once.
Figure 6:
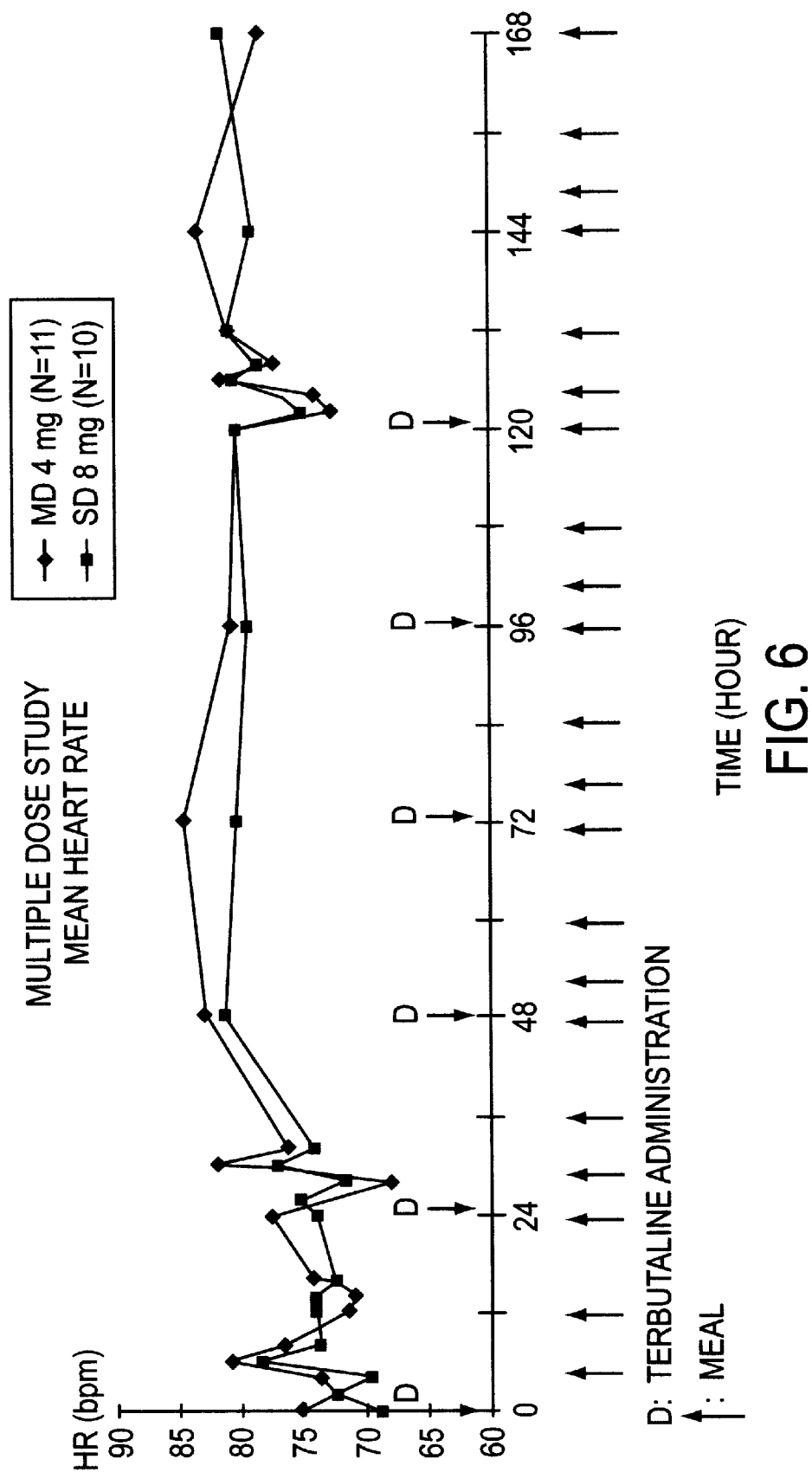
FIG. 6 illustrates mean heart rates in a multiple dose study. Doses were 8 mg, 4 mg, 2 mg, and 1 mg. The terbutaline gel was administered transvaginally once daily for six days.
Figure 7:
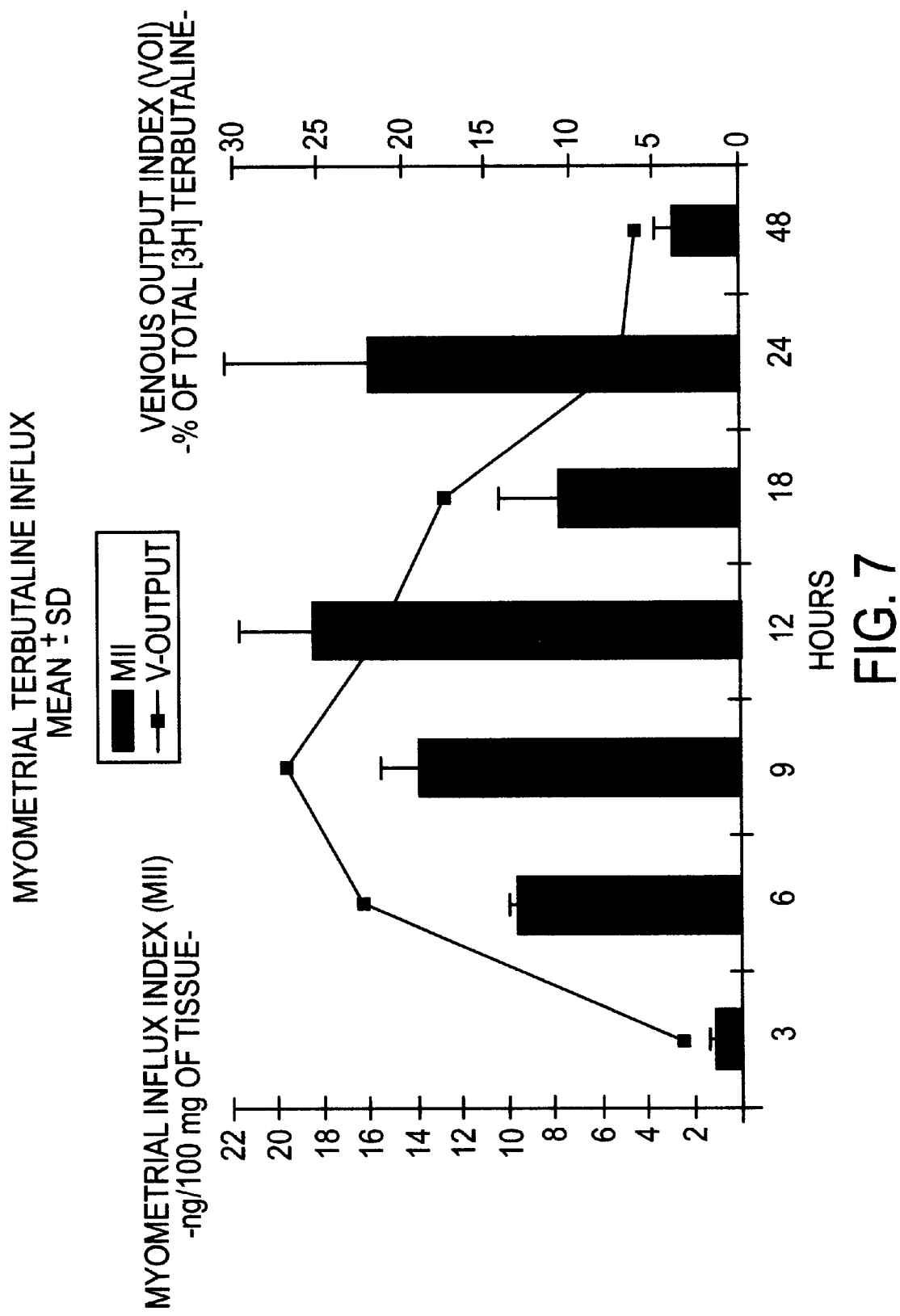
FIG. 7 illustrates the myometrial terbutaline influx in an ex vivo uterine perfusion model.

As can be seen in FIGS. 3 and 4, the serum terbutaline levels in both cases did not reach known levels for toxicity (3000 pg/ml), nor did they even therapeutic concentrations for other conditions such as asthma in the study (1600 pg/ml). A number of patients in the study (40%), however, experienced side effects such as tachycardia at this dose. The occurrence of adverse events at this dose was an unexpected result of the invention, as again the serum levels did not reach known levels for toxicity. This dose can be a method of practicing the invention, but is certainly not the most preferred embodiment.

Example 4

Human Ex Vivo Uterine Perfusion Model

This model verifies the preferential direct delivery of terbutaline from the vagina to the uterus. In this study, uteri obtained from women undergoing hysterectomies for benign diseases were immediately connected to an organ perfusion system in which temperature, $CO_2$ concentration, uterine artery pressure and flow were maintained constant. A perfusion model was opened without recirculation. The direct transfer of terbutaline from the vagina to the uterus was analyzed by applying a mixture of tritiated [$^3$H] terbutaline and unlabeled terbutaline to the cuff of vaginal tissue remaining attached to the cervix after the hysterectomy. Tritiated terbutaline was only used for autoradiography analysis of sections of uterine tissue. The experiments were interrupted at predetermined time intervals after vaginal applications (3 to 12 hours). At the end of the perfusion period, $^3$H and $^{14}$C radioactivity was measured in endometrial and myometrial samples. Tritiated water and $^{14}$C dextran helped to determine that the extend of non-specific vagina to uterus transport (due to leaks of the system) was less than 10%. The myometrial extraction of terbutaline and its corresponding venous outflow during the 12 hour uterine perfusions are shown in FIG. 3 below. The $^3$H terbutaline started to be recovered in the venous effluent uterine during the first 3 hours.

Terbutaline flow was maximal at the 6th–9th hour and then decreased for up to 48 hours of perfusion. Terbutaline flow in the venous effluent uterine is the reflection of terbutaline exiting from the organ. Accumulation of tritiated terbutaline was maximal in the myometrium at 12 hours of perfusion. (Mean±SD of 18.40±3.40 ng/100 mg of tissue) and decreased slowly. Significant accumulation of $^3$H terbutaline still remained at 48 hours of perfusion, with 20% of the original concentration present.

These data demonstrate that a FIRST UTERINE PASS EFFECT® also occurs when terbutaline is delivered vaginally. The nature of the active ingredient and the utilized bioadhesive delivery system of the present invention seem even to be responsible for a more delayed and prolonged delivery of vaginal terbutaline gel than the one described for vaginal progesterone. Indeed, it is unexpected that the maximal myometrial concentration of terbutaline occurred later than that for progesterone. Further, it is notable that terbutaline in the myometrium was shown to last over 48 hours after a single vaginal application. Vaginal terbutaline gel achieves high myometrial concentrations of terbutaline relative to its low systemic concentrations and, consequently, to maximizes utero relaxant effects and minimizes systemic adverse effects.

Any and all publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Reasonable variations, such as those which would occur to a skilled artisan, can be made herein without departing from the spirit and scope of the invention.

We claim:

1. A pharmaceutical composition comprising a therapeutically effective amount of a β-adrenergic agonist together with a pharmaceutically acceptable bioadhesive carrier, wherein the bioadhesive carrier is a cross-linked water-insoluble but water-swellable polycarboxylic acid polymer.

2. The composition of claim 1 wherein the β-adrenergic agonist is terbutaline.

3. A pharmaceutical composition comprising a therapeutically effective amount of a β-adrenergic agonist together with a pharmaceutically acceptable bioadhesive carrier, wherein the β-adrenergic agonist is terbutaline and the bioadhesive carrier is a cross-linked water insoluble but water swellable polycarboxylic acid polymer.

4. The composition of claim 3, wherein the concentration of terbutaline is from 0.1 to 0.4% weight/weight.

5. The composition of claim 4, wherein the polymer is polycarbophil.

6. The composition of claim 5, wherein the β-adrenergic agonist is terbutaline and the composition is prepared so that a dosage of about 1 to 1.5 g of composition will deliver from 1 to 4 mg of terbutaline.

7. A method of preventing or treating dysmenorrhea comprising administering vaginally to a host in need thereof the pharmaceutical composition of claim 1.

8. The method of claim 7, wherein the β-adrenergic agonist is terbutaline and the dosage of composition administered contains from 1 to 4 mg of terbutaline.

9. The method of claim 7, wherein the composition is administered every 12 to 48 hours during dysmenorrhea.

10. The method of claim 7, wherein the composition is administered every 12 to 48 hours beginning one day prior to the anticipated onset of dysmenorrhea and continuing during dysmenorrhea.

11. The method of claim 7, wherein the composition is administered every 24 hours during dysmenorrhea.

12. The method of claim 7, wherein the composition is administered every 24 hours beginning one day prior to the anticipated onset of dysmenorrhea and continuing during dysmenorrhea.

13. A pharmaceutical composition for vaginal administration of a treating agent to other than progesterone, achieve local efficacy without detrimental blood levels of the treating agent, comprising a therapeutically effective amount of said treating agent together with polycarbophil.

14. A method of delivering a treating agent, other than progesterone or an anti-sexually transmitted diseases agent, normally associated with potential undesired side effects at detrimental blood levels to a female subject comprising inserting a bioadhesive, cross-linked water-swellable but water-insoluble polycarboxylic acid polymer formulation with a therapeutically effective amount of said treating agent wherein the formulation releases the treating agent at a rate sufficient to achieve local efficacy without producing detrimental blood levels of the treating agent.

15. A pharmaceutical composition for vaginal administration of a treating agent during menses, comprising polycarbophil and a therapeutically effective amount of a treating agent.

* * * * *

UNITED STATES PATENT AND TRADEMARK OFFICE
CERTIFICATE OF CORRECTION

PATENT NO. : 6,126,959
DATED : October 3, 2000
INVENTOR(S) : LEVINE, et al

It is certified that error appears in the above-identified patent and that said Letters Patent is hereby corrected as shown below:

Column 7, line 8, "NOVEON®-M1" should read --NOVEON®-AA1--

Column 9, line 44, "$t_{1/12}$" should read --$t_{1/2}$--

Column 10, line 22, "$(AU_{o-t})$" should read --$(AUC_{o-t})$--

Column 13, Claim 13, line 2, move "to" from after "agent" to before "achieve" so that the claim reads at the second line: "... of a treating agent other than progesterone, to achieve ..."

Signed and Sealed this

First Day of May, 2001

NICHOLAS P. GODICI

*Attest:*

*Attesting Officer*  *Acting Director of the United States Patent and Trademark Office*